(12) United States Patent
Farr (10) Patent No.: US 6,799,576 B2
(45) Date of Patent: Oct. 5, 2004

(54) SYSTEM FOR EFFECTING SMOKING CESSATION

(75) Inventor: Stephen J. Farr, Orinda, CA (US)

(73) Assignee: Aradigm Corporation, Hayward, CA (US)

(*) Notice: Subject to any disclaimer, the term of this patent is extended or adjusted under 35 U.S.C. 154(b) by 19 days.

(21) Appl. No.: 10/147,390

(22) Filed: May 15, 2002

(65) Prior Publication Data

US 2002/0170566 A1 Nov. 21, 2002

Related U.S. Application Data

(63) Continuation-in-part of application No. 09/611,423, filed on Jul. 7, 2000, now abandoned.
(60) Provisional application No. 60/144,140, filed on Jul. 16, 1999.

(51) Int. Cl.[7] .......................... A61M 16/00; A24F 47/00
(52) U.S. Cl. ....................... 131/271; 131/270; 131/328; 128/200.14; 128/200.12
(58) Field of Search ................................ 131/270, 271, 131/273, 194, 329, 328; 128/202.21, 200.12, 200.14, 200.13, 203.15, 203.12

(56) References Cited

U.S. PATENT DOCUMENTS

| | | |
|---|---|---|
| 4,284,089 A | 8/1981 | Ray |
| 4,393,884 A | 7/1983 | Jacobs |
| 4,474,191 A | 10/1984 | Steiner |
| 4,715,387 A | 12/1987 | Rose |
| 4,735,217 A | 4/1988 | Gerth et al. |
| 4,765,348 A | 8/1988 | Honeycutt |
| 4,793,366 A | 12/1988 | Hill |
| 4,800,903 A | 1/1989 | Ray et al. |
| 4,813,437 A | 3/1989 | Ray |
| 4,917,120 A | 4/1990 | Hill |
| 4,945,929 A | 8/1990 | Egilmex |
| 5,167,242 A | 12/1992 | Turner et al. |
| 5,362,496 A | 11/1994 | Baker et al. |
| 5,400,808 A | 3/1995 | Turner et al. |
| 5,441,060 A | 8/1995 | Rose et al. |
| 5,501,236 A | 3/1996 | Hill et al. |
| 5,721,257 A | 2/1998 | Baker et al. |
| 5,746,227 A | 5/1998 | Rose et al. |
| 5,834,011 A | 11/1998 | Rose et al. |
| 5,894,841 A | 4/1999 | Voges |
| 5,906,202 A | 5/1999 | Schuster et al. |
| 5,935,604 A | 8/1999 | Illum |
| 5,939,100 A | 8/1999 | Albrechtsen et al. |
| 6,024,097 A | 2/2000 | Von Wielligh |
| 6,196,218 B1 * | 3/2001 | Voges ................... 128/200.14 |

FOREIGN PATENT DOCUMENTS

| | | |
|---|---|---|
| WO | WO 99/15171 | 4/1999 |
| WO | WO 99/45902 | 9/1999 |

OTHER PUBLICATIONS

Clarke, (1992) "Nicotine dependence—mechanisms and therapeutic strategies," *Biochem. Soc. Symp.*, 59:83–95.

Henningfield, (1995)"Nicotine Medications for Smoking Cessation," *The New England Journal of Medicine*, 333(18):1196–1203.

* cited by examiner

Primary Examiner—Dionne A. Walls
(74) Attorney, Agent, or Firm—Karl Bozicevic; Bozicevic, Field & Francis LLP (57) ABSTRACT

A system is disclosed which makes it possible for a patient to be delivered gradually reduced amounts of nicotine over time thereby allowing the patient to be gradually weaned off of dependence on nicotine and quit smoking. The system is comprised of a means for aerosolizing a formulation and containers of formulation. The formulation is comprised of nicotine in a pharmaceutically acceptable carrier. Preferably, a plurality of containers are produced wherein the concentration of nicotine in the different containers or different groups of containers is reduced. The patient uses containers with the highest concentration initially and gradually moves towards using containers with lower and lower concentrations of nicotine until the patient's dependence on nicotine is eliminated.

7 Claims, 2 Drawing Sheets

SYSTEM FOR EFFECTING SMOKING CESSATION

CROSS-REFERENCE

This application is a continuation-in-part application of U.S. patent application Ser. No. 09/611,423, filed Jul. 7, 2000 now abandoned and claims the benefit of U.S. Provisional Application No. 60/144,140, filed Jul. 16, 1999, which applications are incorporated herein by reference.

FIELD OF THE INVENTION

This invention relates generally to a method for treating conditions responsive to nicotine therapy. More specifically, the invention relates to pulmonary administration of nicotine to effect smoking cessation.

BACKGROUND OF THE INVENTION

Diseases related to cigarette smoking, such as lung disease, heart disease and cancer, claim an estimated 400,000 lives each year. The combustion of tobacco produces poisons and carcinogens that present a significant health hazard for smokers and non-smokers alike. Nicotine is a principal component of tobacco, and the most pharmacologically active. It is physically addictive, making it extremely difficult for a smoker to quit.

Smoking a cigarette delivers nicotine vapors to the lungs, where nicotine is rapidly absorbed through the arteries and delivered to the brain. Nicotine interacts with nicotinic cholinergic receptors in the brain to induce the release of neurotransmitters and produce an immediate reward—the "rush" that smokers experience—that is associated with a rapid rise in blood level. A persistent stimulus is also produced, and is associated with a high blood level of nicotine. As such, the dopaminergic reward system is activated which eventually results in nicotine dependency. Complex behavioral and social aspects of smoking, e.g., the hand-to-mouth ritual, etc., are also habit-forming.

A therapeutic approach to aid in smoking cessation is to provide the smoker with nicotine from sources other than cigarettes. Nicotine can be administered orally. However, after oral administration it is absorbed from the gut into the portal blood and degraded promptly by the liver. Nicotine can also be administered parenterally, e.g., intravenously, transcutaneously, muscosally, etc. Although preparations of nicotine appropriate for intravenous administration have been available for some time, intravenous cannulation as a means for gaining access to the circulation for the administration of nicotine on demand is not a socially acceptable alternative to cigarette smoking. There are also a number of commercially available nicotine replacement therapies that deliver nicotine to the systemic circulation via absorption through mucosal membranes or the skin. These include nicotine-containing chewing gum, sachets, transdermal patches, capsules, tablets, lozenges, nasal sprays and oral inhalation devices.

In particular, nicotine delivery via inhalation offers the benefit of addressing the psychological component of cigarette smoking in addition to the physiological dependence on nicotine. Nicotine inhalation systems release nicotine as a vapor (see U.S. Pat. Nos. 5,167,242; 5,400,808; 5,501,236; 4,800,903; 4,284,089; 4,917,120; 4,793,366), aerosol (see U.S. Pat. Nos. 5,894,841; 5,834,011) or dry powder (see U.S. Pat. No. 5,746,227) when air is inhaled through the inhaler. A droplet ejection device (U.S. Pat. No. 5,894,841) has also been described that delivers a controlled dose of nicotine via inhalation. These systems deliver low doses of nicotine to the mouth and throat, where nicotine is absorbed through the mucosal membranes into the circulation. Some inhalation therapies feature devices that simulate or approximate the look, feel and taste of cigarettes.

Currently available nicotine replacement therapies, such as transdermal and buccal systems where absorption occurs slowly, provide a low, steady-state blood level of nicotine to the patient without the early nicotine concentration spike that occurs due to immediate, arterial delivery of nicotine to the brain. Thus, the goal of these therapies is to eliminate the immediate, pleasurable effects associated with smoking while still alleviating the nicotine withdrawal effects until complete cessation of nicotine is physically and psychologically possible for the patient. The perceived advantage of these therapies is that the likelihood of abusing the nicotine delivery device (e.g., transdermal patch, nicotine chewing gum, nicotine inhalers, etc.) is very low. However, it is believed by some that it is because of this complete lack of "rush" experienced by the patient, that the success rates of these conventional therapies are not higher than they are.

Thus, the need remains for a smoking cessation therapy that delivers a precise dose of nicotine directly to the lungs and, therefore, directly into the arterial circulation in a profile that mimics the blood levels achieved by cigarette smoking—providing an initial sharp rise in blood level followed by a slow release of nicotine—making it possible for the user to be weaned off of nicotine and to quit smoking.

SUMMARY OF THE INVENTION

A system for aiding a patient in quitting smoking is disclosed. The system is comprised of a means for the delivery of aerosolized nicotine which makes it possible to gradually decrease the amount of nicotine that the patient receives. The system comprises a means for aerosolizing a formulation comprised of nicotine and a means for decreasing the amount of nicotine formulation which is aerosolized and/or the amount which actually reaches the patient's circulatory system. The amount of nicotine aerosolized or effectively delivered to the patient can be changed in several different ways using either the device aerosolization mechanism, the formulation or formulation containers loaded into the device.

A preferred system of the invention aerosolizes the liquid formulation by applying force to a container of nicotine formulation and causing the nicotine formulation to be moved through a porous membrane which results in creating particles of nicotine formulation which are inhaled by the patient. This system modifies the amount of nicotine aerosolized by providing a plurality of different containers or different groups of containers wherein the different containers or groups of containers contain different concentrations of nicotine. A patient using the system can utilize packets of nicotine formulation containing a high concentration initially and then gradually switch towards lower and lower concentrations so that the patient receives essentially the same amount of aerosolized formulation but receives gradually reduced amounts of nicotine due to the reduced concentration of the nicotine in the formulation.

The same procedure described above can also be carried with a dry powder inhaler (DPI). Using the dry powder inhaler technology the packets of dry powder nicotine formulation loaded into the device can initially contain a relatively high concentration of nicotine. Thereafter, the concentration of nicotine in the dry powder formulation added into the device is gradually decreased. Thus, using this system the same amount of dry powder is aerosolized, but the amount of nicotine is gradually decreased by decreasing the concentration or simply the total amount of nicotine in the dry powder package loaded into the device.

Additionally, the same procedure can be utilized with a conventional metered dose inhaler (MDD device. It is somewhat more difficult to utilize the invention with an MDI device. However, small pressurized canisters conventionally used with MDIs can contain different concentrations of nicotine along with the propellant. By using a first container which includes the highest concentration of nicotine and gradually changing to lower and lower concentrations of nicotine in the pressurized canister the desired result of reducing the amount of nicotine delivered to the patient can be obtained. The same results could be obtained by gradually decreasing the amount of formulation released when the value of a container is opened.

When using a dry powder inhaler or a system which aerosolizes a liquid formulation by moving the formulation through a porous membrane, it is possible to decrease the amount of nicotine gradually by making changes in the device, or more specifically the operation of the device. For example, a dry powder inhaler often utilizes a burst of air in order to aerosolize the dry powder. The burst of air could be decreased so that not all of the powder is fully aerosolized or so that the powder is not aerosolized in a completely efficient manner. In a more preferred embodiment the system for aerosolizing liquid formulation is adjusted at different points so that different amount of pressure are applied to the formulation making it possible to aerosolize decreasing amounts of formulation and allowing the patient to be gradually weaned off of nicotine.

The most preferred embodiment of the invention involves the use of a system which aerosolizes liquid formulations of nicotine contained within individual packets which packets include a porous membrane. As indicated above the amount of nicotine that can be changed by changing the amount of or concentration of nicotine in the packets. However, it is also possible to decrease the amount of nicotine actually delivered to the patient's circulatory system by changing the size of the pores in the membrane. When the pore size is in a preferred range then a relatively high concentration of the formulation aerosolized will reach the patient's lungs and move from the lungs into the patient's circulatory system. However, by making the pores larger the aerosolized particles created also become larger. The larger particles will not move into the lungs as efficiently as the smaller particles. Further, the larger particles may be deposited in areas where they are not readily absorbed into the patient's circulatory system.

Thus, in accordance with a preferred embodiment of the invention, a plurality of different containers are produced. The containers are different from each other in that they contain different amounts or concentrations of nicotine. Alternatively, the containers are different from each other in that they have different porous membranes on them which make it possible to aerosolize the formulation in a somewhat less efficient manner over time. It is possible to combine both or all three features together. More specifically, it is possible to produce containers which contain (1) smaller concentrations of nicotine; (2) smaller amounts of nicotine; or (3) have porous membranes which have different size or amounts of pores so as to less efficiently aerosolize the formulation present in the container.

A method for aiding in smoking cessation and for treating conditions responsive to nicotine therapy by the administration of nicotine is disclosed. A formulation comprised of nicotine is aerosolized. The aerosol is inhaled into the lungs of the patient. Once inhaled, particles of nicotine deposit on lung tissue and, from there, enter the patient's circulatory system. Because delivery is to the lungs, rather than to the oral mucosa or through the skin, the nicotine is immediately delivered, along with freshly oxygenated blood, to the heart via the pulmonary arteries where it is then pumped via the aorta to the arterial circulatory system, which is responsible for the delivery of oxygenated blood to the patient's entire body. The carotid arteries, in particular, transport the nicotine-containing oxygenated blood directly to the brain where it is then perfused throughout the brain by the neurovasculature system. Thus, the patient's serum nicotine level in the brain is quickly raised to a desired level—as quickly as if the user were smoking, providing the "rush" effect. The smoker isn't immediately deprived of the psychological pleasures of smoking and, as such, is more likely to successfully complete the smoking-cessation treatment. Because the methods of the invention substantially bypass the body's processes that would effectively metabolize (e.g., by the liver) or dilute (e.g., by systemic distribution via the venous circulatory system) the nicotine dose and thus minimize the effect of the nicotine dose prior to delivery to the brain, the inventive methodologies are able to produce arterial plasma concentrations of nicotine similar to those experienced during cigarette smoking.

Subsequently, the patient's dependence on nicotine is reduced by gradually reducing the dose of nicotine. The dose of nicotine is reduced by progressively increasing the size distribution of the aerosolized nicotine particles delivered to the patient. This decreases the amount of nicotine delivered to the patient's lungs, with the result that nicotine absorption is less immediate and the nicotine blood plasma level is lower.

A method of treatment is disclosed, comprising:
(a) aerosolizing a formulation comprised of nicotine creating aerosolized particles which are sufficiently small as to enter the alveolar ducts;
(b) allowing a patient to inhale the aerosolized particles of (a) thereby causing nicotine to enter the patient's blood at air/blood diffusion membranes;
(c) repeating (a) and (b) a plurality of times;
(d) aerosolizing a formulation comprised of nicotine creating aerosolized particles which are too large to enter alveolar ducts but sufficiently small to enter primary and secondary bronchioles;
(e) allowing the patient to inhale the aerosolized particles of (d) into primary and secondary bronchioles; and
(f) repeating (d) and (e) a plurality of times.

The method is preferably further comprised of:
(g) aerosolizing a formulation comprised of nicotine creating aerosolized particles which are too large to enter primary and secondary bronchioles but sufficiently small to enter the small bronchi;
(h) allowing the patient to inhale the aerosolized particles of (g) into small bronchi; and
(i) repeating (g) and (h) a plurality of times.

Another method of treatment is disclosed which includes the steps of:
(a) aerosolizing a pharmaceutical formulation comprised of nicotine to create aerosolized particles having a size in the range from about 0.5 to 12 ∥; and
(b) allowing the patient to inhale the aerosolized particles of (a) thereby causing nicotine to directly enter the patient's arterial system from the patient's lungs.

The method may further include the step of:

(c) repeating steps (a) and (b) a plurality of times.

In certain embodiments, this method may further include the steps of:

(d) performing step (c) over a first period of time wherein the nicotine is present in a first concentration; and (e) performing step (c) over a second period of time wherein the nicotine is present in a second concentration which is less than the first concentration.

In other embodiments, this method may further include the steps of:

(d) performing step (c) over a first period of time wherein the aerosolized particles have a first size; and (e) performing step (c) over a second period of time wherein the aerosolized particles have a second size which is greater than the first size.

An aspect of the invention is a method of treatment whereby nicotine or a nicotine substitute is aerosolized, inhaled into areas of the respiratory tract including the lungs and provided to the arterial circulatory system of the patient at levels sufficient to simulate cigarette smoking.

An advantage of the invention is that the nicotine levels are raised almost immediately on administration.

Another advantage of the invention is that the patient can gradually be weaned off of the immediate effect of nicotine obtained via smoking and gradually weaned off of the need of nicotine by, respectively, increasing particle size and decreasing dose size or concentration.

A feature of the invention is that aerosolized particles of nicotine having a diameter of about 0.5 to 8 microns ($\mu$) are created and inhaled deeply into the lungs, thereby enhancing the speed and efficiency of administration.

It is an object of this invention to describe the utility of delivering nicotine by inhalation as a means of treating conditions responsive to nicotine therapy, and particularly for smoking cessation therapy.

It is another object of this invention to describe the utility of varying the distribution of aerosolized particles of nicotine inhaled as a means of treating smokers wishing to quit.

It is another object of this invention to describe liquid formulations (which includes suspensions) of nicotine and derivatives thereof appropriate for pulmonary delivery.

It is another object of this invention to describe how nicotine delivered via the lung can quickly increase arterial nicotine blood plasma concentration levels.

An aspect of the invention is a method whereby larger and larger particles of aerosolized nicotine are administered to a patient over time in order to first wean a smoking patient off of the addiction to the immediate effects of nicotine and, thereafter, reduce the amount of nicotine in order to wean the patient completely off of the addiction to nicotine, thereby allowing the patient to quit smoking.

A feature of this invention is that it allows for the formation of nicotine particles in different sizes designed for delivery to different areas of a patient's lungs.

An advantage of the invention is that it allows the patient to be weaned off of (1) the need for immediate nicotine delivery as obtained when smoking, and (2) the need for nicotine at all.

These and other aspects, objects, advantages, and features of the invention will become apparent to those skilled in the art upon reading this disclosure.

DETAILED DESCRIPTION OF THE PREFERRED EMBODIMENTS

Before the devices, formulations, and methodology of the present invention are described, it is to be understood that this invention is not limited to the particular device, components, formulations and methodology described, as such may, of course, vary. It is also to be understood that the terminology used herein is with the purpose of describing particular embodiments only, and is not intended to limit the scope of the present invention which will be limited only by the appended claims.

It must be noted that as used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

Definitions

The term "nicotine" is intended to mean the naturally occurring alkaloid known as nicotine, having the chemical name S-3-(1-methyl-2-pyrrolidinyl)pyridine, which may be isolated and purified from nature or synthetically produced in any manner. This term is also intended to encompass the commonly occurring salts containing pharmacologically acceptable anions, such as hydrochloride, hydrobromide, hydroxide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate, ethanesulfonate, benzenesulfonate, p-toluene sulfonate, camphorate and pamoate salts. Nicotine is a colorless to pale yellow, strongly alkaline, oily, volatile, hygroscopic liquid having a molecular weight of 162.23 and the formula:

Structure and ionisation of nicotine. Nicotine is approximately 10% of the particulate weight in cigarette smoke. Brand differences change this percentage. It is monoprotonated at most physiological pH values. The diprotonated ion would exist at pH values found in the stomach. Metabolism is largely due to oxidation. Cotinine is a major metabolite; however, there are at least 4 primary metabolites of nicotine and all are encompassed by the use of this term herein.

The term "nicotine" further includes any pharmacologically acceptable derivative, metabolite or analog of nicotine which exhibits pharmacotherapeutic properties similar to nicotine. Such derivatives and metabolites are known in the art, and include cotinine, norcotinine, nornicotine, nicotine N-oxide, cotinine N-oxide, 3-hydroxycotinine and 5-hydroxycotinine or pharmaceutically acceptable salts thereof. A number of usefull derivatives of nicotine are disclosed within the Physician's Desk Reference (most recent edition) as well as Harrison's Principles of Internal Medicine. In addition, applicants refer to U.S. Pat. Nos. 5,776,957; 4,965,074; 5,278,176; 5,276,043; 5,227,391; 5,214,060; 5,242,934; 5,223,497; 5,278,045; 5,232,933; 5,138,062; 4,966,916; 4,442,292; 4,321,387; 5,069,094; 5,721,257; all of which are incorporated herein by reference to disclose and describe nicotine derivatives and formulations.

The physiologically active form of nicotine is the S-(-)-isomer. Certain compounds of the present invention may exist in particular geometric or stereoisomeric forms. The present invention contemplates all such compounds, including cis and trans isomers, R and S enantiomers, diastereomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Figure 1:
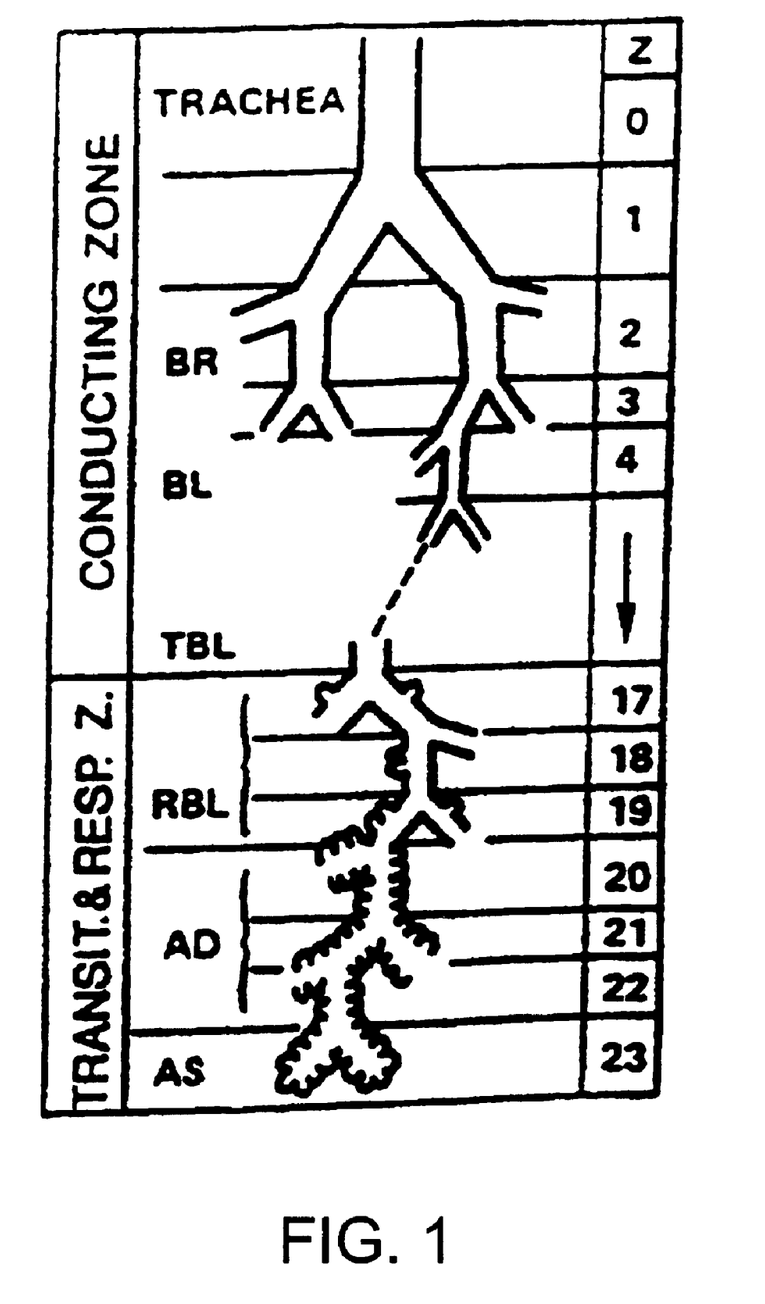
FIG. 1 is a schematic view of a human lung branching pattern.

The term "upper airways" and the like are used interchangeably herein to define an area of the respiratory system which includes the oropharyngeal region and trachea. This area is the first area which air enters upon inhalation (see FIG. 1).

The terms "central airways," "bronchial airways" and the like are used interchangeably herein to refer to a region of the respiratory system that includes generations 1 through 16 of the airways (see FIG. 1) which removes particles larger than $3\mu$ in diameter. They are the conductive airways that also clean particles from the lung using a mucosal clearance mechanism. Upon inhalation, air passes through the upper airways into the central airways.

The terms "pulmonary region," "peripheral region" and the like are used interchangeably herein to define a region of the respiratory system where gas exchange occurs between the lungs and the circulatory system, i.e., where oxygen enters the blood and carbon dioxide leaves the blood. The peripheral region includes generations 17 through 23 of the airways (see FIG. 1). Drugs delivered to this area generally have a systemic effect.

The terms "alveolar ducts," "alveoli" and the like refer to components in the pulmonary region of the lung which are approximately $3\mu$ in diameter where gas exchange occurs between the air in the lungs and the circulatory system.

The term "diameter" is used herein to refer to particle size as given in the "aerodynamic" size of the particle. The aerodynamic diameter is a measurement of a particle of unit density that has the same terminal sedimentation velocity in air under normal atmospheric conditions as the particle in question. This is pointed out in that it is difficult to accurately measure the diameter of small particles using current technology and the shape of such small particles may be continually changing. Thus, the diameter of one particle of material of a given density will be said to have the same diameter as another particle of the same material if the two particles have the same terminal sedimentation velocity in air under the same conditions. In connection with the present invention, it is important that particles, on average, have the desired diameter so that the particles can be inhaled and targeted to a specific area of the lungs. It is also important not to have particles which are too small in that such particles would be inhaled into the lungs and then exhaled without depositing on the lung tissue in the same manner that particles of smoke can be inhaled and exhaled with only a small amount of the particles being deposited on the lung tissue. An acceptable range for particle diameter varies depending on the area of the respiratory tract being targeted. To target the alveolar ducts and alveoli the particles should have a diameter in a range of about $0.5\mu$ to about $2\mu$. To target the area above the alveolar ducts and below the small bronchi the diameter should be in the range of from about $2\mu$ to about $4\mu$ and to target the small bronchi and above the particles should have a diameter of from about $4\mu$ to about $8\mu$.

The term "porous membrane" shall be interpreted to mean a membrane of material in the shape of a sheet having any given outer perimeter shape, but preferably covering a package opening which is in the form of an elongated rectangle, wherein the sheet has a plurality of openings therein, which openings may be placed in a regular or irregular pattern, and which openings have a diameter in the range of $0.25\mu$ to $4\mu$ and a pore density in the range of $1\times10^4$ to about $1\times10^8$ pores per square centimeter. Alternatively, the porous membrane may be merely an area of the package which has pores therein wherein the pores have a size and a density as described above. The configuration and arrangement of the pore density may be changed so as to provide pores which are capable of creating the desired amount of aerosol. For example, the porous membrane or area of the container may have some 10 to 10,000 pores therein which pores are positioned in an area of from about $1 \text{ mm}^2$ to about $1 \text{ cm}^2$. The membrane is preferably comprised of a material having a density in the range of 0.25 to 3.0 mg/cm$^2$, more preferably 1.7 mg/cm$^2$, and a thickness of about $2\mu$ to $20\mu$, more preferably about 8 t to $12\mu$. The membrane material is preferably hydrophobic and includes materials such as polycarbonates and polyesters which may have the pores formed therein by any suitable method including anisotropic etching or by etching through a thin film of metal or other suitable material. Pores can be created in the membrane which may be an area of the container by use of techniques such as etching, plating or laser drilling. The membrane materials may have pores with a conical configuration and have sufficient structural integrity so that it is maintained intact (will not rupture) when subjected to force in the amount of about 20 to 200 psi while the formulation is forced through the pores. The membrane functions to form an aerosolized mist when the formulation is forced through it. Those skilled in the art may contemplate other materials which achieve this function as such materials are intended to be encompassed by this invention.

The terms "treatment," "treating," and the like are used interchangeably herein to generally mean obtaining a desired pharmacological and/or physiological effect. The terms are used in a manner somewhat differently than the terms are typically used in that what is intended by the method of treatment of the invention is to allow a patient to overcome an addiction to nicotine and thereby allow the patient to quit smoking. The treating effect of the invention provides a psychological effect in that the invention originally delivers high doses of nicotine in a manner that simulates the nicotine delivery obtained from a cigarette. The patient then becomes accustomed to relying on the methodology of the invention to provide an immediate "rush" of nicotine. Thereafter, the particles of the aerosol are made larger. This prevents the particles from penetrating deeply into the lung and, therefore, to some extent, diminishes the "rush" of nicotine. However, the same amount of nicotine is still given to the patient in order to satisfy the overall nicotine craving. Eventually, the treatment of the invention reduces the amount of nicotine so as to allow the patient to completely "wean" off of nicotine and to quit smoking.

All publications mentioned herein are incorporated herein by reference to described and disclose specific information for which the reference was cited in connection with. The publications discussed herein are provided solely for their stated disclosure prior to the filing date of the present application. Nothing herein is to be construed as an admission that the invention is not entitled to antedate such publications by virtue of prior invention. Further, the actual publication date may be different from that stated on the publication and as such may require independent verification of the actual publication dates.

General Methodology

The steady state delivery of nicotine as therapy for smokers wishing to quit is characterized by slow absorption and low blood levels of nicotine, which limits its utility. The present invention replaces the nicotine that a smoker receives from smoking a cigarette in a therapeutically effective manner by providing a rapid pulse of bioavailable nicotine to the smoker on demand. More specifically, the present invention provides a treatment methodology wherein a patient's arterial nicotine plasma concentration over a selected time, i.e., the arterial nicotine plasma concentration-rate profile, substantially correlates to that of the patient when smoking a cigarette.

One means currently available for a true pulsatile, rapid onset replacement therapy is intravenous administration. Although preparations of nicotine appropriate for intravenous administration have been available for some time, intravenous cannulation as a means for gaining access to the circulation for the administration of nicotine on demand is not a socially acceptable alternative to cigarette smoking.

The treatment methodology of the present invention creates an aerosol of nicotine particles. The nicotine particles may be formed from any liquid containing nicotine including a solution or suspension of nicotine and aerosolized in any known manner including (1) moving the formulation through a porous membrane in order to create particles or (2) a dry powder where the particles of powder have been designed to have a desired diameter. The rate of particle absorption is directly proportional to the surface area of the tissue on which the particles are deposited. Accordingly, nicotine is absorbed more slowly through the mucosal membranes of the upper respiratory tract which have a smaller surface area than through the airways in the lower respiratory tract which have a larger surface area. Thus, the overall effect of increasing the size of the nicotine particles is to reduce the rate at which nicotine is absorbed into the circulation, thereby reducing the smoker's physiological dependence on the quick rush of nicotine experienced when smoking.

Method of Treatment

The penetration of aerosolized nicotine particles into the respiratory tract is determined largely by the size distribution of the particles formed. Larger particles, i.e., particles with a diameter $\geq 5\mu$ deposit on the upper airways of the lungs (see FIG. 1). Particles having a diameter in a range of about $>2\mu$ to $<5\mu$ penetrate to the central airways. Smaller particles having a diameter $-2\mu$ penetrate to the peripheral region of the lungs.

An important feature of the invention is that the treatment methodology begins with particles of a given size, carries out treatment for a given period of time after which the particles are increased in size. The particles initially administered to the patient penetrate deeply into the lung, i.e., the smallest particles (e.g., 0.5 to $2\mu$) target the alveolar ducts and the alveoli. When the deepest part of the lung is targeted with the smallest particles the patient receives an immediate "rush" from the nicotine delivered which closely matches that received when smoking a cigarette. These small particles can be obtained by milling powder into the desired size and inhaling the powder or by creating a solution or suspension and moving the solution or suspension through the pores of a membrane. In either case, the desired result is to obtain particles which have a diameter in the range of $0.5\mu$ to about $2\mu$. Those skilled in the art will understand that some of the particles will fall above and below the desired range. However, if the majority of the particles (50% or more) fall within the desired range then the desired area of the lung will be correctly targeted.

The patient is allowed to continually, from time to time, target the outermost area of the lung with the smallest particles. For example, the patient would be instructed to repeatedly administer the smallest size particles when the patient would normally smoke a cigarette. In this manner, the patient will become accustomed to finding that the device administers nicotine into the patient in the same manner that a cigarette does. In one embodiment of the invention the concentration of the nicotine in the liquid formulation could be reduced gradually over time. This could be done over a sufficiently long period of time so as to allow the patient to "wean" off of nicotine. However, in a more preferred embodiment of the invention the amount of nicotine is kept substantially constant but the size of the aerosolized particles created are increased.

The second phase of the treatment methodology is to increase the size of the particles so as to target the respiratory tract above the alveolar ducts and below the small bronchi. This can generally be accomplished by creating aerosolized particles of nicotine which have a size and range of about $2\mu$ to about $4\mu$. Administration is carried out in the same manner as described above. Specifically, the patient administers the aerosolized nicotine at the same time when the patient would be smoking a cigarette. Since the patient has become adjusted to receiving the nicotine "rush" from the smaller sized particles, the patient will expect and is therefore likely to experience the same "rush" when administering the slightly larger particles. However, the effect will be less immediate. This procedure is carried out over a period of time, e.g., days or weeks. In one embodiment of the invention it is possible to reduce the dose of aerosolized nicotine delivered to the patient during this second phase. However, the dose may remain constant.

The treatment can be completed after any phase, e.g. after the second phase. However, in accordance with a more preferred embodiment of the invention a third phase of treatment is carried out. Within the third phase the particle size of the aerosolized nicotine is increased again. The particles are increased to a size in a range from about $4\mu$ to about $8\mu$ or, alternatively, perhaps as large as $12\mu$. These larger particles will target the upper airways. The larger particles will give a very small immediate "rush" but will still be absorbed through the mucous membranes of the patient's respiratory tract. Accordingly, the patient will be administering nicotine doses which may be the same as those doses administered at the beginning of treatment. At this point the treatment can take a number of different directions. The patient can attempt to stop administration by immediate and complete cessation of nicotine delivery. Alternatively, the patient can try to wean off of nicotine by delivering fewer doses during a given time period. In another alternative, the same size dose (volume of aerosol formulation) is administered and delivered, creating the same amount of aerosol, but wherein the aerosolized particles contain progressively less nicotine (i.e., more dilute concentration). The amount of nicotine can be decreased until the patient is receiving little or no nicotine. Those skilled in the art reading this disclosure will recognize variations on the overall method and methods for stopping treatment.

There are a number of aspects of the invention which will result in the ability of the smoker to use the invention and, eventually, quit smoking. Firstly, the invention is particularly suited for smokers in that smokers are accustomed to inhaling their source of nicotine. Other treatments such as those involving the transdermal delivery of nicotine via a nicotine "patch" or buckle delivery via a nicotine "gum" do not match the means which a smoker usually obtains nicotine.

Further, the present invention provides a method wherein the patient obtains an influx of nicotine into the circulatory system at a rate which substantially matches the rate which nicotine would enter the circulatory system when smoking. This is obtained because, at least at first, the invention provides sufficiently small particles such that they are inhaled deeply into the lung, i.e. 50% or more of the particles are inhaled deeply into the lung and thereby quickly enter the patient's circulatory system.

Thirdly, the present invention is advantageous in that the rate at which the delivered nicotine enters the circulatory system can be gradually decreased by gradually increasing the size of the aerosolized particles delivered to the patient. This can be done over any desired period of time and in any desired number of phases.

Lastly, the invention provides a means whereby the amount of nicotine delivered to the patient can be gradually decreased in a number of different ways. Firstly, it can be decreased by decreasing the concentration of nicotine in the aerosolized formulation. Secondly, it can be decreased by merely decreasing the number of administrations of aerosolized doses. Thirdly, it can be decreased by decreasing the size of the dose aerosolized and inhaled by the patient. One aspect of the invention is a method of treatment, comprising:
  (a) aerosolizing a formulation comprised of nicotine creating aerosolized particles which are sufficiently small to target a particular lower area of the respiratory tract such as the alveoli. The particles targeting this area will have a relatively small size, e.g. 0.5 micron to about 2 microns in diameter.
  (b) in the next step the patient inhales the aerosolized particles of (a) into the respiratory tract, preferably targeted to a specific area of the lower respiratory tract where the deposited particles cross into the patient's circulatory system.

In step (c), steps (a) and (b) are repeated a plurality of times. Specifically, the patient may repeat these steps any number of times such as every time the patient would normally smoke a cigarette. At this point the patient could continue the treatment protocol in this manner and gradually decrease the number of times the patient administers aerosolized nicotine until the patient is no longer addicted to nicotine. Decreasing the amount of aerosolized nicotine could also be done by decreasing the concentration of nicotine within the aerosolized particles decreasing the concentration of nicotine in the formulation and/or decreasing the size of the aerosolized dose.

Figure 2:
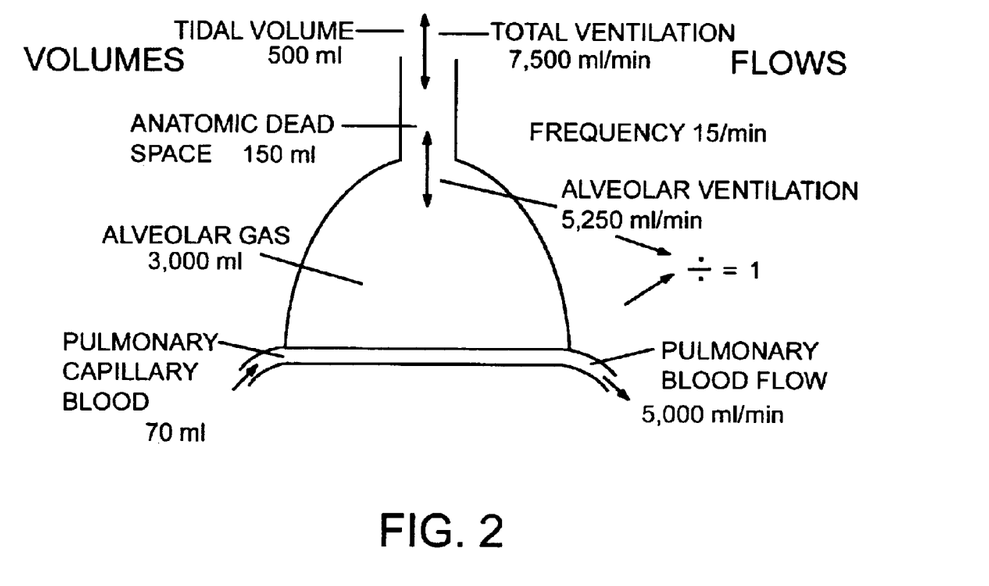
FIG. 2 is a schematic view of a human respiratory tract.

Preferably the method of the invention continues with a step (d) which involves aerosolizing formulation comprised of nicotine in order to create aerosolized particles which are larger in size than the aerosolized particles produced in step (a). These larger particles are directed towards a particular area of the patient's respiratory tract, e.g. the mid-region of the patient's respiratory tract. (See FIGS. 1 and 2) These particles could have a size in the range of about 2 microns to about 4 microns.

In the following step (d) the patient inhales the aerosolized particles of (d) thereby targeting the particular desired area of the patient's respiratory tract such as the mid region. Thereafter, steps (d) and (e) are repeated a plurality of times. At this point the patient can decrease the amount of nicotine being delivered as indicated in the same manner as indicated above step (c). Alternatively, the method of the invention can be continued so that a third phase of treatment can be carried out which phase is similar to the two phases described above. In accordance with the above invention it is possible to carry out the treatment in any number of phases. For example, the treatment could involve as many as 24 phases which target specific defined regions of a patients respiratory tract using particles which are continually larger in size in each of the 24 phases (see FIG. 1 and Table 1 below). Because it may not be practical to specifically design the particles so that they are all larger in each of the phases the formulations may be designed so that a certain percentage of the particles within each phase of delivery is larger than the particles in the preceding phase.

The method of the invention can be carried out using 1 to 24 different phases with each phase targeting a higher level of the respiratory tract (See Table 1). The higher levels of the respiratory tract can be targeted using larger and larger particles.

TABLE 1

Subdivision of the Respiratory Tree

| Generation | Name |
| --- | --- |
| 0 | Trachea |
| 1 | Primary bronchi |
| 2 | Lobar bronchi |
| 3 | Segmental bronchi |
| 4 | subsegmental bronchi |
| 5 | Small bronchi |
| ↓ | |
| 10 | |
| 11 | Bronchioles, primary and secondary |
| ↓ | |
| 13 | |
| 14 | Terminal bronchioles |
| ↓ | |
| 15 | |
| 16 | Respiratory bronchioles |
| ↓ | |
| 18 | |
| 19 | Alveolar ducts |
| ↓ | |
| 23 | |
| 24 | Alveoli |

Nicotine Delivery Devices

Precision delivery of small molecule drugs via the lung for systemic effect is possible. An electronic inhaler capable of delivering a liquid formulated drug stored in a unit dose packages has been described and disclosed in U.S. Pat. No. 5,718,222 entitled "Disposible Package for Use in Aerosolized Delivery of Drugs," and is incorporated herin by reference. A formulation of nicotine can be prepared for delivery with this system. Quantitative delivery of nicotine on demand provides a mechanism for nicotine replacement therapy which is unlikely to be associated with recidivism precipitated by the symptoms of physical withdrawal.

In the present invention, a nicotine formulation is forced through the openings or pores of a porous membrane to create an aerosol. In the preferred embodiment, the openings are all uniform in size and are positioned at uniform distances from each other. However, openings can be varied in size and randomly placed on the membrane, If th size of the openings is varied, the size of the particles formed will also vary. In general, it is preferable to maintain uniform opening sizes in order to create uniform particle sizes, and it is particularly preferable to have the opening sizes within the range of about $0.25\mu$ to about $6\mu$ which will create particle sizes of about $0.5\mu$ to $12\mu$ which are preferred with respect to inhalation applications. When the openings have a pore size in the range of $0.25\mu$ to $1\mu$ they will produce an aerosol having particle sizes in the range of $0.5\mu$ to $2\mu$, which is particularly useful for delivering nicotine to the alveolar ducts and alveoli. Pore sizes having a diameter of about $1\mu$ to $2\mu$ will produce particles having a diameter of about $2\mu$ to $4\mu$ which are particularly useful for delivering nicotine to the area above the alveolar ducts and below the small bronchi. A pore size of $2\mu$ to $4\mu$ will create particles having a diameter of of $4\mu$ to $8\mu$, which will target the area of the respiratory tract from the small bronchi upward.

Increasing the size of the openings of the porous membranes produces nicotine particles of increasing size. A strategy in which the blood level of nicotine is reduced gradually will be the most effective in treating the symptoms of withdrawal, and thereby increase the chances of successful smoking cessation. In one embodiment of the invention, the size of the aerosolized nicotine particles is increased in a stepwise manner by using porous membranes that create "monodisperse" aerosols, wherein all the particles within the aerosol created have essentially the same particle size. Nicotine particles of increasing size are produced by using membranes of increasing pore sizes.

In another embodiment, the size of the aerosolized nicotine particles is increased in gradient fashion by using porous membranes that create "multi-disperse" aerosols, wherein the particles within the aerosol created have different particle sizes. Membranes which have an increasing range of pore sizes are used to produce nicotine particles of increasing size.

Nicotine can be administered orally. However, after oral administration it is absorbed from the gut into the portal blood and degraded promptly by the liver. Thus, insignificant amounts reach the patient's systemic circulation. Nicotine can also be administered parenterally. However, when so administered it is rapidly absorbed and metabolized making it difficult to sustain therapeutic levels in plasma over time. In view of such, effective therapy has been carried out using other means of delivery (e.g., transdermal patches, gum). The present invention uses intrapulmonary delivery to avoid first pass liver metabolism and to obtain quick infusion into the arterial side of the patient's systemic circulatory system. The present invention administers sufficient nicotine by inhalation to temporarily produce a rapid increase in the patient's blood level, and thereafter allow the patient's nicotine level to return to a therapeutically effective level.

Because intrapulmonary administration is not 100% efficient, the amount of drug aerosolized will be greater than the amount that actually reaches the patient's circulation. For example, if the inhalation system used is only 50% efficient then the patient will aerosolize a dose which is twice that needed to raise the patient's nicotine level to the extent needed to obtain the desired results. More specifically, when attempting to administer 1 mg of nicotine with a delivery system known to be 50% efficient, the patient will aerosolize an amount of formulation containing about 2 mg of nicotine.

A device comprised of a container that includes an opening covered by a porous membrane, such as the device disclosed in U.S. Pat. No. 5,906,202, may be used to deliver nicotine. The device may be designed to have the shape and/or bear the markings of a pack of cigarettes, and may include the scent of tobacco. These features and others that address the behavioral component of cigarette smoking may enhance the effectiveness of the method described herein.

Dosing

Cigarettes contain 6 to 11 mg of nicotine, of which the smoker typically absorbs 1–3 mg; see Henningfield *N Engl J Med* 333:1196–1203 (1995). Factors influencing nicotine absorption include subject-dependent factors, such as smoking behavior, lung clearance rate, etc., morphological factors, and physiological factors, such as tidal volume, inspiratory and expiratory flow rate, particle size and density. See Darby et al., *Clin Pharmacokinet* 9:435–439 (1984). The systemic dose of nicotine per puff is extremely variable, however, peak plasma concentrations of 25–40 ng/mL of nicotine, achieved within 5–7 minutes by cigarette smoking, are believed typical. In accordance with the present invention, 0.1 mg to 10 mg, preferably 1 to 3 mg, and more preferably about 2 mg of nicotine are delivered to the lungs of the patient in a single dose to achieve peak blood plasma concentrations of 15–40 ng/mL.

The amount of a nicotine administered will vary based on factors such as the age, weight and frequency of smoking or nicotine tolerance of the smoker. Other factors, such as daily stress patterns, demographic factors may also determine, in part, the amount of nicotine sufficient to satisfy the smoker's craving for nicotine. Administering nicotine using the methods of the present invention can involve the daily administration of anywhere from 5 mg to 200 mg of nicotine, but more preferably involves the administration of approximately 10 to 100 mg per day.

It is noted that nicotine can be administered in toxic amounts. Care should be taken not to overdose the patient. The amount of nicotine which an individual can tolerate will vary on a number of factors including size, sex, weight and amount of cigarette smoking the patient is accustomed to. In order to avoid overdosing it is possible to program a lock-out system into the delivery device which prevents administration of aerosolized doses beyond a given point. Such a system is described within U.S. Pat. No. 5,735,263 issued Apr. 7, 1998 and incorporated herein by reference in its entirety to disclose drug delivery devices and lock-out systems used in connection therewith.

The nicotine is in a liquid form or is dissolved or dispersed within a pharmaceutically acceptable, liquid excipient material to provide a liquid, flowable formulation which can be readily aerosolized. The container will include the formulation having nicotine therein in an amount of about 10 mL to 300 mL, more preferably about 200 mL. The large variation in the amounts which might be delivered is due to different delivery efficiencies for different devices. Administration may involve several inhalations by the patient, with each inhalation providing nicotine from the device. For example, the device can be programmed so as to release the contents of a single container or to move from one container to the next on a package of interconnected containers. Delivering smaller amounts from several containers can have advantages. Since only small amounts are delivered from each container and with each inhalation, even a complete failure to deliver nicotine with a given inhalation is not of great significance and will not seriously disturb the reproducibility of the dosing event. Further, since relatively small amounts are delivered with each inhalation, the patient can safely administer a few additional micrograms (or milligrams) of nicotine without fear of overdosing.

In one embodiment of the invention the patient is treated in the three different phases. In the first phase the aerosolized liquid particles or dry powder particles have a size and a range of $0.5\mu$ to about $2\mu$. The particles of nicotine having this size are administered in a dosage amount which is substantially equivalent to the doses or amount which the patient would received from a single cigarette or, alternatively, the dosage amount which the patient would received from a single puff on a single cigarette. Assuming that the patient receives the dosage amount of a single cigarette then the patient will be administered approximately 1 to 3 mg of nicotine each time the formulation is aerosolized. The particles having a size of $0.5\mu$ to about $2\mu$ will be administered to the patient over a plurality of days (e.g., 2 to 7 days) or perhaps a plurality of weeks (e.g., 2 to 4 weeks). If the device and/or dosage containers are designed to deliver a dosage equivalent to a puff on a cigarette then substantially smaller doses are delivered. If each dose corresponds to a puff on a cigarette then a patient may be directed to continually take aerosolized doses equivalent to a cigarette puff over a period of one to ten minutes or any period of time equivalent to what that patient normally takes to smoke one cigarette. This constitutes the first phase of treatment.

After completing the first phase of the treatment the method of the invention may be completed. However, as indicated above the method may be continued by repeating phases such as the first phase using continually larger particles and/or continuing more dilute solutions of nicotine and/or smaller doses of nicotine.

Within the second phase of treatment the patient is preferably administered the same dosage amount of nicotine with each inhalation, e.g., the patient is administered 1 to 3 mg of nicotine each time formulation is aerosolized. However, during the second phase the size of the particles is increased to a size and range from $2\mu$ to about $4\mu$. The particle size is increased in order to target an area of the lungs where the nicotine will be absorbed into the circulatory system more slowly. Specifically, the larger particles target an area of the lungs above the alveolar ducts and below the small bronchi. Administration is carried out over a plurality of days or a plurality of weeks in the same manner as indicated above. Within all phases the patient preferably administers nicotine from a device of the invention when the patient would normally smoke a cigarette. The treatment can be completed pursuant to the present invention by using only the two phases. However, it is preferable to include three or more phases.

In accordance with the third phase, the same dose is administered each time nicotine formulation is aerosolized. Accordingly, 1 to 3 mg of nicotine is delivered to the patient at each dose. However, the dose is delivered by using aerosolized particles which have a diameter of $4\mu$ or more, e.g., in the range of from $4\mu$ to about $8\mu$. These larger particles are designed to target the area of the respiratory tract at the small bronchi or higher. When the nicotine targets the upper airways it will not immediately enter the patient's circulatory system. However, the nicotine will, eventually, cross the mucous membranes of the upper respiratory tract and enter the circulatory system. Thus the patient will be administered nicotine but will become less accustomed to having the immediate "rush" obtained from smoking. Thus, within the third phase the patient has been weaned away from the need for the "rush" of nicotine. The third phase is then used to continually reduce the number of administrations needed and thereby reduce the amount of nicotine administered. By this process the patient's dependency on nicotine is slowly reduced and then eliminated thereby allowing the patient to quit smoking.

When nicotine enters the circulatory system of a human patient it is oxidized to cotinine within four to six hours. The present invention includes the administration of cotinine and other nicotine derivatives provided such derivatives do not result in unacceptable adverse effects.

Indications

The method of the invention has applicability to smokers wishing to quit or trying to quit who have experienced all or any of the nicotine withdrawal symptoms associated with smoking cessation, such as craving for nicotine, irritability, mood ability, frustration or anger, anxiety, drowsiness, sleep disturbances, impaired concentration, nervousness, restlessness, decreased heart rate, increased appetite and weight gain.

While particularly applicable to smoking cessation, pulmonary administration of nicotine could be of value for the treatment of other diseases, such as for patients suffering from neurodegenerative diseases, psychiatric disorders and other central nervous system disorders responsive to nicotinic receptor modulation (see U.S. Pat. Nos. 5,187,169; 5,227,391; 5,272,155; 5,276,043; 5,278,176; 5,691,365; 5,885,998; 5,889,029; 5,914,328). Such diseases include, but are not limited to, senile dementia of the Alzheimer's type, Parkinson's disease, schizophrenia, obsessive-compulsive behavior, Tourette's Syndrome, depression, attention deficit disorder, myasthenia gravis and drug addiction.

Formulations

Pharmaceutical grade nicotine can be produced as a colorless to pale yellow liquid. The pure liquid could be aerosolized and inhaled by itself. Alternatively, a formulation may include a buffer to enhance absorption. Any absorption enhancers including ammonia could be used with the formulation. However, a typical formulation is only nicotine dissolved in water or dry powder nicotine. Methods of formulating liquids and liquid inhalers are disclosed in U.S. Pat. Nos. 5,364,838; 5,709,202; 5,497,763; 5,544,646; 5,718,222; 5,660,166; 5,823,178; and 5,910,301; all of which are incorporated by reference to describe and disclose such. Formulations of nicotine include aqueous formulations, aqueous saline formulations, and ethanol formulations. All of these formulations may be included with additional components such as permeation enhancers, buffers, preservatives and excipient and carrier components and additives normally included within formulations for aerosolized drug delivery.

Nicotine is freely soluble in water. An aqueous nicotine solution may be readily aerosolized and inhaled. The nicotine solution can be placed in a low boiling point propellant in a pressurized canister and released using a conventional metered dose inhaler (MDI) device. Preferably, the MDI device is modified so that the aerosolized dose is released each time at the same inspiratory flow rate and inspiratory volume. When this is done the patient is more likely to receive the same dose each time. A device for obtaining repeating dosing with an MDI canister is taught in U.S. Pat. No. 5,404,871.

In accordance with the present invention it is preferable to load the nicotine solution into a container which opens to a porous membrane. When the formulation is forced through the membrane it is aerosolized. Such a container is taught in U.S. Pat. No. 5,497,763 and is loaded into a device and delivered via a method as taught in U.S. Pat. No. 5,823,178. Both patents are incorporated herein by reference to describe and disclose containers, devices and methods of drug delivery by inhalation.

A dry powder formulation comprising a pharmacologically acceptable salt of nicotine alone or with additives such as components to prevent the particles from sticking together may be used.

Supplememtal Treatment Methodology

Smokers wishing to quit may be treated solely with respiratory nicotine as indicated above, i.e. by intrapulmonary delivery. However, it is possible to treat such patients with a combination of pulmonary administration and other means of administration, such as transdermal administration. Transdermal nicotine is preferably administered to maintain a steady state level of nicotine within the circulatory system. Nasal or buccal formulation could be used for nasal or buccal delivery which could supplement aerosolized delivery.

Based on the above, it will be understood by those skilled in the art that a plurality of different treatments and means of administration can be used to treat a single patient. For example, a patient can be simultaneously treated with nicotine by transdermal administration, nicotine via pulmonary administration, in accordance with the present invention, and nicotine which is administered to the mucosa.

The instant invention is shown and described herein in a manner which is considered to be the most practical and preferred embodiments. It is recognized, however, that departures may be made therefrom which are within the scope of the invention and that obvious modifications will occur to one skilled in the art upon reading this disclosure.

What is claimed is:

1. A method of treatment, comprising the steps of:
    (a) providing a system comprising:
        a device for creating aerosolized particles and configured to receive a container containing a pharmaceutical formulation to be aerosolized;
        a plurality of groups of containers for use with the device, wherein each container within a group of containers contains a pharmaceutical formulation having the same concentration of nicotine and wherein each group of containers contains a pharmaceutical formulation having concentration of nicotine different from each of the other groups of containers;
    (b) over a first period of time, repeatedly using the device with a first group of containers to aerosolize the pharmaceutical formulation; and
    (c) over a second period of time, repeatedly using the device with a second group of containers to aerosolize the pharmaceutical formulation, wherein the concentration of nicotine in the second group of containers is less than the concentration of nicotine in the first group of containers.

2. The method of claim 1, further comprising:
    over any number of subsequent periods of time, using the device with successive groups of containers wherein the concentration of nicotine in the subsequently used groups of containers is gradually reduced with each group of containers used.

3. The method of claim 1 wherein the concentration of nicotine used during the first period of time is sufficient to produce an arterial nicotine plasma concentration within the patient which substantially corresponds to that achieved during cigarette smoking.

4. The method of claim 1 wherein the particles have a size in the range from about 0.5 to 12 µm.

5. A method of treatment, comprising the steps of:
    (a) providing a system comprising:
        a device for creating aerosolized particles and configured to receive a container containing a pharmaceutical formulation to be aersolized;
        a plurality of groups of containers for use with the device, wherein each container within a group of containers contains a pharmaceutical formulation having the same concentration of nicotine and wherein each group of containers contains a pharmaceutical formulation having concentration of nicotine different from each of the other groups of containers;
    (b) using the device with a first container of a first group of containers containing a pharmaceutical formulation having a first concentration of nicotine to aerosolize the pharmaceutical formulation;
    (c) allowing the patient to inhale the aerosolized particles of (b) thereby causing nicotine to directly enter the patient's arterial system from the patient's lungs;
    (d) repeating steps (b) and (c) once for any number of other containers of the first group of containers; and
    (e) repeating step (d) for any number of other groups of containers wherein the concentration of nicotine in the subsequently used groups of containers is gradually reduced.

6. The method of claim 5 wherein the concentration of nicotine used during the first occurrence of step (b) is sufficient to produce an arterial nicotine plasma concentration within the patient which substantially corresponds to that achieved during cigarette smoking.

7. The method of claim 5 wherein the particles have a size in the range from about 0.5 to 12 µm.

* * * * *